United States Patent
Bowman et al.

(10) Patent No.: US 9,120,906 B2
(45) Date of Patent: *Sep. 1, 2015

(54) AZEOTROPE-LIKE COMPOSITIONS OF TETRAFLUOROPROPENE AND ALCOHOLS

(71) Applicant: HONEYWELL INTERNATIONAL INC., Morristown, NJ (US)

(72) Inventors: James M. Bowman, Geneva, IL (US); Rajiv R. Singh, Getzville, NY (US); David J. Williams, East Amherst, NY (US); Hang T. Pham, Amherst, NY (US); Justin L. Becker, Orchard Park, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/340,828

(22) Filed: Jul. 25, 2014

(65) Prior Publication Data

US 2014/0336291 A1    Nov. 13, 2014

Related U.S. Application Data

(63) Continuation of application No. 13/371,811, filed on Feb. 13, 2012, now Pat. No. 8,791,167, which is a continuation of application No. 11/787,304, filed on Apr. 16, 2007, now Pat. No. 8,114,828.

(51) Int. Cl.
| | |
|---|---|
| *C08J 9/14* | (2006.01) |
| *C09K 3/30* | (2006.01) |
| *C09K 5/04* | (2006.01) |
| *C11D 7/50* | (2006.01) |

(52) U.S. Cl.
CPC ........ *C08J 9/149* (2013.01); *C08J 9/142* (2013.01); *C08J 9/146* (2013.01); *C09K 3/30* (2013.01); *C09K 5/045* (2013.01); *C11D 7/5081* (2013.01); *C08J 2203/12* (2013.01); *C08J 2203/182* (2013.01); *C08J 2207/04* (2013.01); *C08J 2325/06* (2013.01); *C08J 2375/04* (2013.01); *C09K 2205/102* (2013.01); *C09K 2205/126* (2013.01); *C09K 2205/32* (2013.01)

(58) Field of Classification Search
CPC ............ C08J 2203/12; C08J 2203/182; C08J 2207/04; C08J 2325/06; C08J 2375/04; C08J 9/142; C08J 9/146; C08J 9/149; C09K 2205/102; C09K 2205/126; C09K 2205/32; C09K 3/30; C09K 5/045; C11D 7/5081
USPC ............ 521/131, 146, 155, 170, 180; 252/67; 510/412, 415
See application file for complete search history.

(56) References Cited

U.S. PATENT DOCUMENTS

| | | | | |
|---|---|---|---|---|
| 8,114,828 | B2 * | 2/2012 | Bowman et al. | 510/412 |
| 8,791,167 | B2 * | 7/2014 | Bowman et al. | 521/131 |
| 2004/0256594 | A1 * | 12/2004 | Singh et al. | 252/71 |
| 2006/0211782 | A1 * | 9/2006 | Handa et al. | 521/79 |

* cited by examiner

*Primary Examiner* — John Cooney
(74) *Attorney, Agent, or Firm* — Colleen D. Szuch

(57) ABSTRACT

A composition including an effective amount of trans-1,3,3,3-tetrafluoropropene component combined with an effective amount of an alcohol selected from the group of methanol, ethanol, propanol, isopropanol, tert-butanol, isobutanol, 2-ethyl hexanol and any combination thereof, where the composition has azeotropic properties.

14 Claims, No Drawings

AZEOTROPE-LIKE COMPOSITIONS OF TETRAFLUOROPROPENE AND ALCOHOLS

CROSS-REFERENCE TO RELATED APPLICATIONS

This application is a Continuation of U.S. application Ser. No. 13/371,811, filed on Feb. 13, 2013, which application is a Continuation of U.S. application Ser. No. 11/787,304, filed on Apr. 16, 2007, now Pat. No. 8,114,828, issued on Feb. 14, 2012, the disclosures of which are incorporated herein by reference.

BACKGROUND OF THE INVENTION

1. Field of the Invention

The present disclosure is related to azeotrope-like compositions of trans-1,3,3,3-tetrafluoropropene and alcohols, and uses thereof.

2. Description of Related Art

Fluorocarbon based fluids have found widespread use in industry in a number of applications, including as refrigerants, aerosol propellants, blowing agents, heat transfer media, and gaseous dielectrics. Due to the suspected environmental problems associated with the use of some of these fluids, especially the relatively high global warming potentials associated therewith, it is desirable to use fluids having low or even zero ozone depletion potential, such as hydrofluorocarbons ("HFCs"). Thus, the use of fluids that do not contain chlorofluorocarbons ("CFCs") of hydrochloroflourocarbons ("HCFCs") is desirable. Additionally, the use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable.

Accordingly, there is a need for single component fluids or mixtures that overcome, alleviate, and/or mitigate one or more of the aforementioned and other deleterious effects of prior art fluids and mixtures.

BRIEF SUMMARY OF THE INVENTION

This disclosure provides a composition that comprises an effective amount of trans-1,3,3,3-tetrafluoropropene combined with an effective amount of an alcohol selected from the group of methanol, ethanol, propanol, isopropanol, tert-butanol, isobutanol, 2-ethyl hexanol, and any combination thereof, where the composition has azeotropic properties.

In some embodiments, the composition has an alcohol component that ranges from greater than 0 to about 25 weight percent, and the trans-1,3,3,3-tetrafluoropropene component ranges from about 75 to less than 100 weight percent. The composition of the present disclosure can have a boiling point from about −20° C. to about −19° C. at a pressure of about 14.3 psia.

In some aspects, the composition of the present disclosure further comprises a thermoset foam component, where the composition is a blowing agent for the thermoset foam component, and the thermoset foam component comprises a composition selected from the group consisting of polyurethane foam, polyisocyanurate foam, phenolic foam and any combinations thereof.

In some aspects, the composition of the present disclosure further comprises a thermoplastic foam component, where the composition is a blowing agent for the thermoplastic foam component, and the thermoplastic foam component is selected from the group consisting of polystyrene, polyethylene, polypropylene, polyethyleneterephthalate, and any combinations thereof.

The present disclosure also discloses an aerosol comprising an effective amount of trans-1,3,3,3-tetrafluoropropene combined with an effective amount of an alcohol selected from the group of methanol, ethanol, propanol, isopropanol, tert-butanol, isobutanol, 2-ethyl hexanol, and any combination thereof.

Also disclosed in the present disclosure is a process of forming a foam, that comprises the combining of an effective amount of trans-1,3,3,3-tetrafluoropropene with an effective amount of an alcohol selected from the group of methanol, ethanol, propanol, isopropanol, tert-butanol, isobutanol, 2-ethyl hexanol, and any combination thereof, to form a blowing agent. The blowing agent is added to a foamable composition to form a mixture. The mixture is reacted under conditions effective to form a cellular structure. The blowing agent can be added to the foamable composition directly or indirectly.

In some aspects, the foamable composition is a thermoset foam component, selected from the group consisting of polyurethane foam, polyisocyanurate foam, phenolic foam and any combinations thereof.

In some aspects, the foamable composition is a thermoplastic foam component selected from the group consisting of polystyrene, polyethylene, polypropylene, polyethyleneterephthalate, and any combinations thereof.

The foamable composition can include an A-side and a B-side, wherein the B-side is a formulated polyol blend formed from components selected from the group consisting of a polyol, a surfactant, a catalyst, an adjuvant, and any combination thereof, and wherein the A-side is isocyanate. The blowing agent can be added to the A-side prior to combining the A-side and the B-side. The blowing agent can also be added to the B-side prior to combining the A-side and the B-side. In some aspects, the blowing agent is added to the foamable composition during formation of the foam. In some embodiments, the A-side, the B-side, and the blowing agent are combined using a foam head. In all the above-described aspects, the blowing agent can form cells in the cellular structure that results.

The present disclosure further provides a process of forming an azeotropic-like composition that comprises the combining of an effective amount of trans-1,3,3,3-tetrafluoropropene to an effective amount of an alcohol selected from the group of methanol, ethanol, propanol, isopropanol, tert-butanol, isobutanol, 2-ethyl hexanol, and any combination thereof, wherein a substance having azeotropic properties is formed. In some embodiments, the trans-1,3,3,3-tetrafluoropropene and the alcohol are combined using a method selected from the group consisting of mixing, blending, contacting by hand, contacting by machine, batch reaction, continuous reaction, and any combination thereof.

It is another object to provide a method of cooling an article that includes condensing a composition having an effective amount of trans-1,3,3,3-tetrafluoropropene combined with an effective amount of an alcohol selected from the group of methanol, ethanol, propanol, isopropanol, tert-butanol, isobutanol, 2-ethyl hexanol and any combination thereof, where the composition can have azeotropic properties. A condensation step is followed by the evaporation of the composition in the vicinity of the article to be cooled.

The above-described and other features and advantages of the present disclosure will be appreciated and understood by those skilled in the art from the following detailed description and appended claims.

DETAILED DESCRIPTION OF THE PREFERRED EMBODIMENTS

The present disclosure provides several compositions that help to satisfy the continuing need for alternatives to CFCs and HCFCs. According to certain embodiments, the present disclosure provides azeotrope-like compositions comprising trans-1,3,3,3-tetrafluoropropene ("trans-HFO-1234ze") and alcohols such as methanol ("MeOH"), ethanol ("EtOH"), propanol ("PA"), isopropanol ("IPA"), 2-ethyl hexanol ("2-EH") and any combination thereof.

In some aspects, the alcohol component of the azeotropic-like composition of the present disclosure ranges from greater than 0 to about 25 weight percent, and the trans-1,3,3,3-tetrafluoropropene component ranges from about 75 to less than 100 weight percent. In some aspects, the alcohol component ranges from greater than 0 to about 20 weight percent, and the trans-1,3,3,3-tetrafluoropropene component ranges from about 80 to less than 100 weight percent. In some aspects, the alcohol component ranges from about 2 to about 15 weight percent, and the trans-1,3,3,3-tetrafluoropropene component ranges from about 85 to about 98 weight percent.

In some aspects, the composition of the present disclosure has a boiling point from about −20° C. to about −19° C. at a pressure of about 14.3 psia, or the composition has a boiling point of from about −19.5° C. to about −19° C. at a pressure of about 14.3 psia.

The compositions described in the disclosure tend to exhibit relatively low global warming potentials ("GWPs"). Accordingly, it has been recognized by the current disclosure that such compositions can be used in a number of applications, including, but not limited to a replacement for CFCs, HCFCs, and HFCs (such as HFC-134a) in refrigerant, aerosol, blowing agents and other applications.

Additionally, the current disclosure supplies the surprising azeotrope-like compositions of trans-HFO-1234ze and alcohols, such as MeOH, EtOH, PA, IPA, 2-EH, and any combination thereof, which can be formed. Accordingly, in other embodiments, the present disclosure provides methods of producing an azeotrope-like composition comprising combining trans-HFO-1234ze and alcohols in amounts effective to produce a composition that in some aspects has azeotropic properties.

In addition, applicants have recognized that the azeotrope-like compositions of the present disclosure exhibits properties that make them advantageous for use as, or in, refrigerant, aerosol, and blowing agent compositions. Accordingly, in yet other embodiments, the present disclosure provides refrigerant compositions comprising an azeotrope-like composition of trans-1,3,3,3-tetrafluoropropene and alcohols.

As used herein, the term "azeotrope-like" is intended in its broad sense to include both compositions that are strictly azeotropic and compositions that behave like azeotropic mixtures, e.g., compounds with azeotropic properties. In some applications the composition of the present disclosure retains the azeotropic properties, but in some applications the compound of the present disclosure is non-azeotropic. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

The azeotrope-like compositions of the disclosure may include additional components that do not form new azeotrope-like systems, or additional components that are not in the first distillation cut. The first distillation cut is the first cut taken after the distillation column displays steady state operation under total reflux conditions. One way to determine whether a composition is azeotropic or has azeotropic properties is to distill a sample of the composition with the component under conditions that would be expected to separate a non-azeotropic mixture into its separate components. If the mixture is azeotrope-like, some finite amount of a first distillation cut will be obtained that contains all of the mixture components that is constant-boiling or behaves as a single substance.

It follows from this that another characteristic of azeotrope-like compositions is that there is a range of compositions containing the same components in varying proportions that are azeotrope-like or constant-boiling. All such compositions are intended to be covered by the terms "azeotrope-like" and "constant-boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein, i.e., contain azeotropic properties.

It is well-recognized in the art that it is not possible to predict the formation of azeotropes. However, this disclosure provides an unexpected azeotropic or azeotropic-like composition that is formed from an effective amount of trans-1,3,3,3-tetrafluoropropene and an effective amount of an alcohol, or combination of alcohols.

According to certain preferred embodiments, the azeotrope-like compositions of the present disclosure comprise effective amounts of trans-1,3,3,3-tetrafluoropropene and alcohols. The term "effective amounts" as used herein refers to the amount of each component which upon combination with the other component, results in the formation of an azeotrope-like composition of the present disclosure.

The azeotrope-like compositions of the present disclosure can be produced by combining effective amounts of trans-1,3,3,3-tetrafluoropropene and alcohols. Any of a wide variety of methods known in the art for combining two or more components to form a composition can be adapted for use in the present methods to produce an azeotrope-like composition. For example, trans-1,3,3,3-tetrafluoropropene and EtOH can be mixed, blended, or otherwise contacted by hand and/or by machine, as part of a batch or continuous reaction and/or process, or via combinations of two or more such steps. In light of the disclosure herein, those of skill in the art will be readily able to prepare azeotrope-like compositions according to the present disclosure without undue experimentation.

The present compositions have utility in a wide range of applications. For example, embodiments of the present disclosure relate to blowing agents, aerosols, cleaning agents, and refrigerant compositions that comprise the present azeotrope-like compositions.

One embodiment of the present disclosure relates to methods of forming thermoset foams, and preferably polyurethane and polyisocyanurate foams. The methods generally comprise providing a blowing agent composition of the present disclosure, adding (directly or indirectly) the blowing agent composition to a foamable composition, and reacting the foamable composition under the conditions effective to form a foam or cellular structure. These foams may be open cell or closed cell. Any of the methods well known in the art may be used or adapted for use in accordance with the foam embodiments of the present disclosure.

In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above.

It is also possible to produce thermoplastic foams using the compositions of the present disclosure. For example, conventional polystyrene and polyethylene formulations may be combined with the compositions in a conventional manner to produce rigid foams. Examples of thermoplastic foam components include polyolefins, such as for example polystyrene. Other examples of thermoplastic resins include polyethylene, ethylene copolymers, polypropylene, and polyethyleneterephthalate. In certain embodiments, the thermoplastic foamable composition is an extrudable composition. It is also generally recognized that the thermoplastic foamable composition may include adjuvants such as nucleating agents, flame or fire retardant materials, cell modifiers, cell pressure modifiers, and the like.

With respect to thermoplastic foams, the preferred methods generally comprise introducing a blowing agent in accordance with the present disclosure into a thermoplastic material, and then subjecting the thermoplastic material to conditions effective to cause foaming. For example, the step of introducing the blowing agent into the thermoplastic material may comprise introducing the blowing agent into a screw extruder containing the thermoplastic, and the step of causing foam may comprise lowering the pressure on the thermoplastic material and thereby causing expansion of the blowing agent and contributing to the foaming of the material.

It will be generally appreciated by those skilled in the art, especially in view of the disclosure herein, that the order and manner in which the blowing agent of the present disclosure is formed and/or added to the foamable composition, or the components that form the foamable composition, does not generally affect the operability of the thermoset or the thermoplastic foams of the present disclosure.

Illustrative of this is thermoset plastics where the blowing agent composition may be added together, or separately, wherein the azeotropic composition exists in the blowing agent stream, or in the case wherein the trans-HFO-1234ze, or alternately, the alcohol is added to a masterbatch of B-side (polyol blend), and the other co-blowing agent is added to the B-side as a separate stream by means of a shear mixer as a third stream, directly at the foam head, or as an additive in the A-side (isocyanate). It should be noted that the blowing agent used in the formation of thermoset or thermoplastic foams, or any foam, does not necessarily retain azeotropic properties in every application, but it is a mixture of an effective amount of trans-1,3,3,3-tetrafluoropropene combined with an effective amount of an alcohol selected from the group of methanol, ethanol, propanol, isopropanol, tert-butanol, isobutanol, 2-ethyl hexanol, and any combination thereof. In some aspects, the blowing agent of this disclosure does retain azeotropic properties.

Another example is extruded thermoplastics where the blowing agent composition maybe added together, or at separate locations in the extruder, or as one co-blowing agent encapsulated in the resin bead, with the other co-blowing agent added to the extruder into the plastic melt.

In a polyol pre-mix, one of the co-agents, and more preferably the alcohol, is added to a fully formulated pre-mix, with the other co-agent added to the fully formulated polyol premix during the foaming process, or to the A-side, prior to the foaming process, such that one embodiment of the composition claimed herein is formed in the foam or foam cells. It is immaterial in this illustration whether one or more of the blowing agent compositions exist in the cell, adhered to the cell wall, or dissolved into the polymer matrix.

It is contemplated also that in certain embodiments it may be desirable to utilize the present compositions when in the supercritical or near supercritical state as a blowing agent.

The refrigerant compositions of the present disclosure may be used in any of a wide variety of refrigeration systems including air-conditioning, refrigeration, heat-pump systems, and the like. In certain embodiments, the compositions of the present disclosure are used in refrigeration systems originally designed for use with an HFC-refrigerant, such as, for example, HFC-134a. The compositions of the present disclosure tend to exhibit many of the desirable characteristics of HFC-134a and other HFC-refrigerants, including non-flammability, and a GWP that is as low, or lower than that of conventional HFC-refrigerants. In addition, the relatively constant boiling nature of the compositions of the present disclosure makes them even more desirable than certain conventional HFCs for use as refrigerants in many applications.

In certain other preferred embodiments, the present compositions are used in refrigeration systems originally designed for use with a CFC-refrigerant. Refrigeration compositions of the present disclosure may be used in refrigeration systems containing a lubricant used conventionally with CFC-refrigerants, such as mineral oils, silicone oils, and the like, or may be used with other lubricants traditionally used with HFC refrigerants.

In certain embodiments, the compositions of the present disclosure may be used to retrofit refrigeration systems containing HFC, HCFC, and/or CFC-refrigerants and lubricants used conventionally therewith. Preferably, the present methods involve recharging a refrigerant system that contains a refrigerant to be replaced and a lubricant comprising the steps of (a) removing the refrigerant to be replaced from the refrigeration system while retaining a substantial portion of the lubricant in the system; and (b) introducing to the system a composition of the present disclosure. As used herein, the term "substantial portion" refers generally to a quantity of lubricant which is at least about 50% (by weight) of the quantity of lubricant contained in the refrigeration system prior to removal of the chlorine-containing refrigerant. Preferably, the substantial portion of lubricant in the system according to the present disclosure is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Any of a wide range of known methods can be used to remove refrigerants to be replaced from a refrigeration system while removing less than a major portion of the lubricant contained in the system. For example, because refrigerants are quite volatile relative to traditional hydrocarbon-based lubricants (the boiling points of refrigerants are generally less than 10° C. whereas the boiling points of mineral oils are generally more than 200° C.), in embodiments wherein the lubricant is a hydrocarbon-based lubricant, the removal step may readily be performed by pumping chlorine-containing refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove chlorine-containing lubricants from refrigeration systems and to provide a refrigeration system having therein a hydrocarbon-based lubricant and substantially no chlorine-containing refrigerant according to the present disclosure.

Any of a wide range of methods for introducing the present refrigerant compositions to a refrigeration system can be used in the present disclosure. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging methods can be used.

According to certain other embodiments, the present disclosure provides refrigeration systems comprising a refrigerant of the present disclosure and methods of producing heating or cooling by condensing and/or evaporating a composition of the present disclosure. In certain preferred embodiments, the methods for cooling an article according to the present disclosure comprise condensing a refrigerant composition comprising an azeotrope-like composition of the present disclosure and thereafter evaporating the refrigerant composition in the vicinity of the article to be cooled. Certain preferred methods for heating an article comprise condensing a refrigerant composition comprising an azeotrope-like composition of the present disclosure in the vicinity of the article to be heated and thereafter evaporating the refrigerant composition.

In another embodiment, the azeotrope-like compositions of this disclosure may be used as propellants in sprayable compositions, either alone or in combination with known propellants. The propellant composition comprises of the azeotrope-like compositions of this disclosure. In some embodiments, additional elements can be added to the azeotropic-like compositions form a propellant. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, defluxing agents, and polishing agents as well as medicinal materials such as anti-asthma and anti-halitosis medications.

Yet another embodiment of the present disclosure relates to a blowing agent comprising one or more azeotrope-like compositions of the disclosure. In other embodiments, the disclosure provides foamable compositions, and preferably polyurethane and polyisocyanurate foam compositions, and methods of preparing foams. In such foam embodiments, one or more of the present azeotrope-like compositions are included as a blowing agent in a foamable composition, which composition preferably includes one or more additional components capable of reacting and foaming under the proper conditions to form a foam or cellular structure. Any of the methods well known in the art may also be used or adapted for use in accordance with the foam embodiments and methods of the present disclosure.

In some aspects, a process of forming a thermoset foam can include combining an effective amount of trans-1,3,3,3-tetrafluoropropene with an effective amount of an alcohol selected from the group of methanol, ethanol, propanol, isopropanol, tert-butanol, isobutanol, 2-ethyl hexanol, and any combination thereof, to form a blowing agent that in some aspects has azeotropic properties. It should be noted that in some applications the blowing agent(s) of the present disclosure do not have azeotropic properties, as the components of a foam application cause the blowing agent to not have azeotropic properties. The blowing agent is added to a foamable composition to form a mixture, and the mixture is reacted under conditions effective to form a cellular structure. In some embodiments, the blowing agent is added indirectly to the foamable composition.

In some aspects, the foamable composition comprises an A-side and a B-side, wherein the B-side is a formulated polyol blend formed from components selected from the group polyol(s), surfactant(s), catalyst(s), adjuvant(s), and any combination thereof, and the A-side is isocyanate. The blowing agent is added to the A-side prior to combining the A-side and the B-side, or the blowing agent is added to the B-side prior to combining the A-side and the B-side, wherein the blowing agent forms cells in the cellular structure of the thermoset foam. In some aspects, the blowing agent is added to the foamable composition during formation of the thermoset foam. The A-side, the B-side, and the blowing agent can also be combined using a foam head. In some aspects, the blowing agent is added to the fully formulated poylol blend, the isocyanate—or A-side, or as a third stream during the foaming process to the A-side, B-side, or directly at the foam head. The B-side composition and A-side is brought together, mixed by an appropriate methods—usually foam head, and dispensed into the application, wherein the reaction occurs, and the blowing agent forms the cells in the plastic foam.

Other uses of the presently disclosed azeotrope-like compositions include, but are not limited to, use as solvents, cleaning agents, and the like. Those of skill in the art will be readily able to adapt the present compositions for use in such applications without undue experimentation.

The disclosure is further illustrated in the following examples, which are intended to be illustrative, but not limiting in any manner.

Example 1 provides an ebulliometer consisting of vacuum jacketed tube with a condenser on top which is further equipped with a Quartz Thermometer. About 23.5 g trans-HFO-1234ze is charged to the ebulliometer and then EtOH is added in small, measured increments. Temperature depression is observed when EtOH is added to trans-HFO-1234ze, indicating a binary minimum boiling azeotrope is formed. From greater than about 0 to about 20 weight percent EtOH, the boiling point of the composition stays below or around the boiling point of trans-HFO-1234ze. The binary mixtures shown in Table 1 were studied and the boiling point of the compositions did not go above the boiling point of trans-HFO-1234ze. The compositions exhibit azeotrope and/or azeotrope-like properties over this range.

TABLE 1 trans-HFO-1234ze/EtOH compositions at 14.3 psia:

| T (C.) | Wt. % Trans-1234ze | Wt. % EtOH |
|---|---|---|
| −19.02 | 100.00 | 0.00 |
| −19.02 | 99.83 | 0.17 |
| −19.03 | 99.48 | 0.52 |
| −19.03 | 99.14 | 0.86 |
| −19.12 | 98.80 | 1.20 |
| −19.13 | 98.13 | 1.87 |
| −19.13 | 97.46 | 2.54 |
| −19.14 | 96.16 | 3.84 |
| −19.14 | 94.90 | 5.10 |
| −19.13 | 93.06 | 6.94 |
| −19.12 | 91.29 | 8.71 |
| −19.12 | 89.59 | 10.41 |
| −19.11 | 87.41 | 12.59 |
| −19.11 | 85.34 | 14.66 |
| −19.09 | 83.37 | 16.63 |

Example 2 demonstrates a blowing agent performance comprising about 92% by weight of trans-1,3,3,3-tetrafluoropropene and 8% by weight of ethanol for polystyrene foam formed in a twin screw type extruder. The apparatus employed in this example is a Leistritz twin screw extruder having the following characteristics:

30 mm co-rotating screws
L:D Ratio=40:1
Die: 5.0 mm rod (circular)

The extruder is divided into 10 sections, each representing a L:D of 4:1. The polystyrene resin was introduced into the first section, the blowing agent was introduced into the sixth section, with the extrudate exiting the tenth section through the die. The extruder operated as a melt/mixing/cooling extruder.

Polystyrene resin, namely Nova Chemical—general extrusion grade polystyrene, identified as Nova 1600, is fed to the extruder under the conditions indicated above. The resin has a recommended melt temperature of 375° F.-525° F. The pressure of the extruder at the die is about 1350 pounds per square inch (psi), and the temperature at the die is about 130° C.

A blowing agent is added to the extruder at the location indicated above, with about 0.5% by weight of talc being included, on the basis of the total blowing agent, as a nucleating agent. Foam is produced using the blowing agent at concentrations of 8.7% by weight and 10.7% by weight in accordance with the present disclosure. The density of the foam produced is in the range of about 0.07 grams per cubic centimeter to 0.08 grams per cubic centimeter, with a cell size of about 300 to about 700 microns. The foams, of approximately 30 millimeters diameter, are visually of very good quality, fine cell size, with no visible or apparent blow holes or voids.

Further foam extrusions, under similar process conditions, with blowing agent concentration of about 10.7% by weight, without nucleating agent, yielded foams with cell size of about 600 to about 1500 microns.

TABLE 2

Extrusion processing conditions for trans-HFO-1234ze/EtOH (92 weight %/8 weight %)

| Blowing agent | Blowing Agent Composition (%) | Blowing Agent Pressure (psi) | Die Pressure (psi) | Melt Temp. (° C.) | Density (g/cc) |
|---|---|---|---|---|---|
| 8/92 ethanol/1234ze | 10.7 | 520 | 1300-1400 | 132.7 | 0.078 |
| 8/92 ethanol/1234ze | 8.7 | 700 | 1400 | 130.8 | 0.07 |
| 8/92 ethanol/1234ze | 10.7 | 750 | 1350 | 129.5 | 0.1 |

TABLE 3

Cell size measurement for trans-HFO-1234ze/EtOH (92 weight %/8 weight %) in PS foam.

| Blowing agent | Density (g/cc) | Cell size, cross section (micron) | Cell size, machine direction (micron) |
|---|---|---|---|
| 8/92 ethanol/1234ze | 0.07 | 457 | 324 |
| 8/92 ethanol/1234ze (no talc) | 0.1 | 1454 | 648 |

Example 3 provides an ebulliometer consisting of vacuum jacketed tube with a condenser on top which is further equipped with a quartz thermometer. About 20 g trans-HFO-1234ze is charged to the ebulliometer and then MeOH is added in small, measured increments. Similar to Example 1 above, a minimal boiling azeotrope is found at 5-6 wt % MeOH and 94-95 wt % trans-HFO-1234ze. Azeotropic-like range is found till about 20 wt % MeOH and 80 wt % trans-HFO-1234ze.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A blowing agent comprising an azeotrope-like composition consisting essentially of trans-1,3,3,3-tetrafluoropropene and ethanol, wherein said trans-1,3,3,3-tetrafluoropropene and ethanol are present in an amount effective to form an azeotrope-like composition, and wherein said azeotrope-like composition has a boiling point of from about −20° C. to about −19° C. at a pressure of about 14.3 psia.

2. The blowing agent of claim 1, wherein said trans-1,3,3,3-tetrafluoropropene is present in said azeotrope-like composition in amounts of from about 83 to about 98 weight percent of said azeotrope-like composition.

3. The blowing agent of claim 2, wherein said trans-1,3,3,3-tetrafluoropropene is present in said azeotrope-like composition in amounts of from about 83.4 weight percent to about 98.8 weight percent of said composition.

4. The blowing agent of claim 1, wherein said ethanol is present in said azeotrope-like composition in amounts of from about 1 to about 16 weight percent of said azeotrope-like composition.

5. The blowing agent of claim 4, wherein said ethanol is present in said azeotrope-like composition in amounts of from about 1.2 to about 16.6 weight percent of said azeotrope-like compositions.

6. A method of forming a foamable composition comprising the steps of:
  (i) providing at least one thermoplastic foam forming component;
  (ii) providing a blowing agent composition comprising an azeotrope-like compoposition consisting essentially of trans-1,3,3,3-tetrafluoropropene and ethanol, wherein said trans-1,3,3,3-tetrafluoropropene and ethanol are present in an amount effective to form an azeotrope-like composition, and wherein said azeotrope-like composition has a boiling point of from about −20° C. to about −19° C. at a pressure of about 14.3 psia; and
  (iii) forming a foamable composition by combining said thermoplastic foam forming component and said blowing agent composition.

7. A method of forming a thermoplastic foam comprising forming a foam from the foambable compositon formed according to claim 6.

8. The method of claim 7, further comprising volatilizing said azeotrope-like composition during said forming.

9. The method of claim 6, wherein said trans-1,3,3,3-tetrafluoropropene is present in said azeotrope-like composition in amounts of from about 83 to about 98 weight percent of said azeotrope-like composition.

10. The method of claim 6, wherein said trans-1,3,3,3-tetrafluoropropene is present in said azeotrope-like composition in amounts of from about 83.4 to about 98.8 weight percent of said azeotrope-like composition.

11. The method of claim 6, wherein said ethanol is present in said azeotrope-like composition in amounts of from about 1 to about 16 weight percent of said azeotrope-like composition.

12. The method of claim 6, wherein said ethanol is present in said azeotrope-like composition in amounts of from about 1.2 to about 16.6 weight percent of said azeotrope-like composition.

13. The method of claim 6, wherein said thermoplastic foam component is selected from the group consisting of polystyrene, polyethylene, polypropylene, polyethyleneterephthalate, and combinations of two or more of these.

14. The method of claim 6, wherein said thermoplastic foam component comprises polystyrene.

* * * * *